United States Patent [19]

Schinzel et al.

[11] Patent Number: 4,814,453

[45] Date of Patent: Mar. 21, 1989

[54] NAPHTHALIMIDES CONTAINING SULFURIC ACID ESTER GROUPS, A PROCESS FOR THEIR PREPARATION AND THEIR USE

[75] Inventors: Erich Schinzel, Hofheim am Taunus; Thomas Martini, Kelkheim, both of Fed. Rep. of Germany

[73] Assignee: Hoechst Aktiengesellschaft, Frankfurt am Main, Fed. Rep. of Germany

[21] Appl. No.: 55,904

[22] Filed: May 29, 1987

[30] Foreign Application Priority Data

Jun. 2, 1986 [DE] Fed. Rep. of Germany ....... 3618458

[51] Int. Cl.$^4$ .................... C07D 221/14; D06L 3/12
[52] U.S. Cl. ........................................... 546/98; 8/648
[58] Field of Search ......................................... 546/98

[56] References Cited

FOREIGN PATENT DOCUMENTS 185273  9/1980  Czechoslovakia .
962019  6/1964  United Kingdom ................. 546/98
2127015 4/1984  United Kingdom ................. 546/98

OTHER PUBLICATIONS

"Methoden der Organischen Chemie (Houben-Weyl)", vol. IX, p. 441, (1955).

*Primary Examiner*—Mark L. Berch

[57] ABSTRACT

New optical brighteners of the general formula

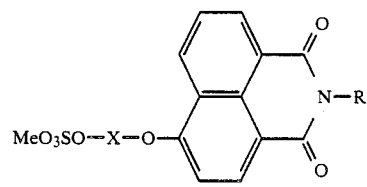

in which
R denotes hydrogen, alkyl, alkoxyalkyl, cyclohexyl, methylcyclohexyl, benzyl, phenylethyl, phenyl, alkylphenyl or xylyl,
X denotes a $C_2$–$C_7$-alkylene group or a bridge member of the formula —$X^1$—$(OX^2)_n$— in which $X^1$ and $X^2$ denote $C_2H_4$ or $C_3H_7$ and n denotes 1 or 2 and Me denotes a proton, an alkali metal cation or a cation $NH_2R^1R^2$ in which $R^1$ and $R^2$ represent hydrogen, alkyl or hydroxyalkyl.

2 Claims, No Drawings

NAPHTHALIMIDES CONTAINING SULFURIC ACID ESTER GROUPS, A PROCESS FOR THEIR PREPARATION AND THEIR USE

It is already known to use naphthalimides containing sulfonic acid groups as optical brighteners. Thus, for example, salts of N-(β-sulfoethyl)-4-methoxynaphthalimide are described as optical brighteners in Czechoslovakian Patent No. 185,273.

The present invention relates to compounds of the general formula (1)

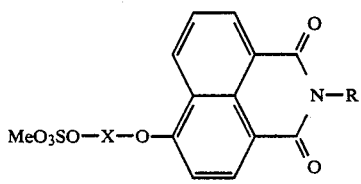

in which

R denotes hydrogen, alkyl, alkoxyalkyl, cyclohexyl, methylcyclohexyl, benzyl, phenylethyl, phenyl, alkylphenyl or xylyl, X denotes a $C_2$-$C_7$-alkylene group or a bridge member of the formula $-X^1-(OX^2)_n-$ in which $X^1$ and $X^2$ denote $C_2H_4$ or $C_3H_7$ and n denotes 1 or 2 and Me denotes a proton, an alkali metal cation, or a cation $NH_2R^1R^2$ in which $R^1$ and $R^2$ represent hydrogen, alkyl or hydroxyalkyl.

Compounds of the formula (1) of particular importance are those in which R denotes hydrogen, $C_1$-$C_4$-alkyl or benzyl, X denotes $C_2$-$C_5$-alkylene and Me denotes a proton, an alkali metal cation or a cation $-NH_2R^1R^2$ in which $R^1$ and $R^2$ represent hydrogen, $C_1$-$C_2$-alkyl or $C_1$-$C_2$-hydroxyalkyl.

Unless otherwise defined, alkyl and alkoxy groups contain 1 to 6, preferably 1 to 4, carbon atoms.

The compounds of formula (1) can be prepared by introducing the hydroxyl compounds of the general formula (2)

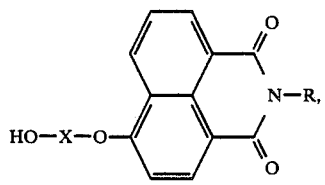

(2), in which R and X have the meaning indicated above, into concentrated sulfuric acid at temperatures of 0°-30° C., preferably 5°-10°, and stirring the mixture for 1 to 4 hours at this temperature until a homogeneous solution is formed. The mixture is worked up by being poured onto ice water and neutralized with concentrated sodium hydroxide solution, filtered off with suction, after cooling with ice the sodium sulfate decahydrate which has crystallized out, and rinsed with ice water. The Na salt of the sulfuric acid ester (1) is precipitated in the filtrate, for example by salting out with sodium chloride, and is filtered off with suction and washed free from sulfate with sodium chloride solution.

The compounds of the general formula (2) can be prepared by subjecting 4-chloronaphthalic anhydride to a condensation reaction with 1 mole of an amine (R—NH₂) in a lower alcohol at temperatures of 50°-80° C. for 4 to 10 hours and subsequently reacting the 4-chloronaphthalimide (3) obtained

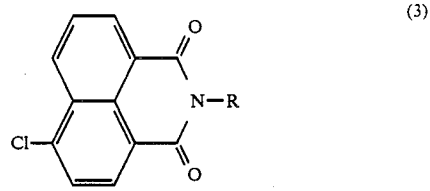

with a solution of a monosodium salt of the formula NaO—X—OH in an excess of the corresponding diol at 100° to 110° C. for 3 to 10 hours. This solution can be obtained by stirring 1 mole of a methanolic solution of sodium methylate with excess diol at room temperature and subsequently removing the methanol in vacuo at 60°-70° C.

The following are examples of amines R—NH₂ which can be employed:

ammonia, methylamine, ethylamine, n-propylamine, isopropylamine, 3-methoxypropylamine, n-butylamine, isobutylamine, tert.-butylamine, n-hexylamine, cyclohexylamine, 4-aminohexahydrotoluene, aniline, 3-aminotoluene, 4-aminotoluene, benzylamine, 1-amino-4-ethylbenzene, p-tert.-butylaniline, β-phenylethylamine, 4-amino-1,2-xylene, 4-amino-1,3-xylene, 4-amino-1-isopropylbenzene.

The following are examples of diols HO—X—OH which can be employed:

ethylene glycol, propane-1,2-diol, propane-1,3-diol, n-butane-1,3-diol, n-butane-1,3-diol, n-butane-2,3-diol, 2,2-dimethylpropane-1,3-diol, 2,2'-diethylpropane-1,3-diol, pentane-1,5-diol, n-hexane-2,5-diol, n-hexane-1,6-diol, 2,3-dimethyl-n-butane-2,3-diol, diethylene glycol and triethylene glycol.

In a dissolved or finely divided state, the new compounds according to the invention exhibit, to a varying extent, a pronounced fluorescence. They are used for optically brightening various synthetic, semi-synthetic or natural organic materials.

Without intending any limitation thereto in the review following, the following groups of organic materials may be mentioned as examples of the above:

(1) polymerization products, for example polymers based on α, β-unsaturated carboxylic acids or derivatives of such carboxylic acids, in particular on acrylic compounds or on olefin hydrocarbons, and polymers based on vinyl and vinylidene compounds, (2) polymerization products which can be obtained by ring opening, for example polyamides of the polycaprolactam type, and also polymers which can be obtained either via polyaddition or via polycondensation, such as polyethers or polyacetals, (3) polycondensation products or precondensates based on bifunctional or polyfunctional compounds containing groups capable of condensation and homocondensation and co-condensation products thereof, such as, for example, polyesters, in particular saturated polyesters (for example ethylene glycol terephthalic acid polyesters) and unbranched and branched polyesters (including those based on polyhydric alcohols, such as (for example, alkyd resins) and polyamides (for example hexamethylenediamine adipate), (4) semi-synthetic organic materials, for example cellulose esters of varying degrees of esterification (so-called 2½-acetate or triacetate), cellulose ethers or regenerated cellulose, and (5) natural organic materials of animal or vegetable origin, for example those based on cellulose or proteins, such as cotton, wool, linen and silk.

Preferred organic materials are those based on polyamide and wool.

The organic materials to be optically brightened can be in a very wide range of states of processing (raw materials, semi-finished goods or finished goods).

Fiber materials can, for example, be in the form of continuous filaments (stretched or unstretched), staple fibers, flocks, hanks, textile threads, yarns, twists, nonwoven fabrics, felts, waddings, flocked structures or textile woven fabrics or composite textile materials or knitted fabrics and papers, cardboards or paper compositions.

Inter alia, the compounds to be used in accordance with the invention are of importance for treating textile organic materials, in particular textile woven fabrics.

If fibers, which can be in the form of staple fibres or continuous filaments or in the form of hanks, woven fabrics, knitted fabrics, non-woven fabrics, flocked substrates or composite materials, are to be optically brightened in accordance with the invention, this is advantageously effected in an aqueous medium in which the compounds concerned are present in a dissolved or finely divided form (suspensions or so-called microdispersions). If appropriate, dispersion agents, stabilizers, wetting agents and further auxiliaries can be added in the course of the treatment.

Depending on the type of brightening compound used, it can prove advantageous to carry out the process in a neutral or alkaline or acid liquor. The treatment is usually carried out at temperatures from about 20° to 140° C., for example at the boiling point of the liquor or near to this temperature (for instance 90° C.). Solutions or emulsions in organic solvents are also suitable for finishing textile substrates in accordance with the invention, as is practiced in the dyeing industry in so-called solvent dyeing (pad-thermofix application or exhaustion dyeing processes in dyeing machines).

The new optical brighteners according to the present invention can also be added to or incorporated in the materials before they are shaped or while they are being shaped. Thus they can, for example, be added to the compression molding material or injection molding material in the production of films, sheeting (for example milling into polyvinyl chloride under hot conditions) or molded articles.

The new optical brighteners according to the present invention can, for example, also be employed in the following use forms:

(1) mixtures with dyestuffs (shading) or pigments or as an additive to dyebaths, printing pastes, discharge pastes or reserve pastes. Also for the after-treatment of dyeings, prints or discharge prints, (2) in mixtures with so-called carriers, wetting agents, softening agents, swelling agents, antioxidants, light stabilizers, heat stabilizers and, particularly, chemical bleaching agents (chlorite bleaches or additives for bleaching baths), (3) in a mixture with crosslinking agents or finishing agents (for example starch or synthetic finishes) and in combination with a very wide variety of textile finishing processes, in particular synthetic resin finishes, and also flame-retarding, soft handle, soil-repellent or antistatic finishes or antimicrobial finishes, and (4) in combination with other substances having an optically brightening action.

In certain cases the full effect of the brighteners is obtained by means of an after-treatment. This can, for example, be a chemical treatment (for example acid treatment), a thermal treatment (for example heat) or a combined chemical/thermal treatment.

The amount of the new optical brighteners to be used in accordance with the invention, relative to the material to be optically brightened, can vary within wide limits. A pronounced and durable effect can be achieved even with very small amounts, in certain cases, for example, amounts of 0.0001% by weight. For most practical requirements amounts between 0.01 and 0.5% by weight are preferably of interest.

The brighteners according to the invention can also be employed as a mixture with other brighteners. Since some of the brighteners according to the invention produce brightening effects having a green shade, it is particularly advantageous to use them together with brighteners which display red-tinged brightening effects.

The new optical brighteners have the particular advantage that they are effective even in the presence of active chlorine donors, such as, for example, hypochlorite, and can be used without essential loss of effect in washing baths containing non-ionogenic washing agents, for example alkylphenol polyglycol ethers.

Unless otherwise indicated, parts in the examples are always parts by weight and percentages are always percentages by weight. Unless a note is made to the contrary, melting points and boiling points are uncorrected.

PREPARATION EXAMPLES

4-Chloronaphthalimides (Table 1)

255.6 g of 91% strength 4-chloronaphthalic anhydride are suspended in 2.4 liters of methanol in a 5-liter stirred autoclave, 75.94 g of 40.9% strength methylamine solution are added, and the mixture is stirred for 4 hours at 70° C. After cooling, the product is filtered off with suction at room temperature and the material on the filter is washed with methanol until the runnings are colorless. Drying is carried out at 60° C. in vacuo. This gives 223.8 g of compound (11), which, after recrystallization from toluene, has a constant melting point of 172°–175°.

The 4-chloronaphthalimides listed in Table 1 are obtained analogously using ethanol or n-butanol as the solvent and with reaction times of up to 9 hours.

TABLE 1

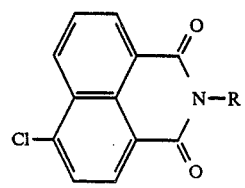

| No. | R | Melting point °C. | Purifying agent |
|---|---|---|---|
| (11) | —CH$_3$ | 172–175 | toluene |
| (12) | —(CH$_2$)$_3$CH$_3$ | 93–95 | ethanol |
| (13) | —(CH$_2$)$_3$OCH$_3$ | 84–88 | ethyl acetate |

TABLE 1-continued

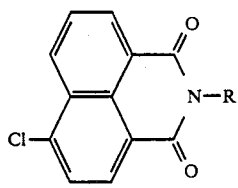

| No. | R | Melting point °C. | Purifying agent |
|---|---|---|---|
| (14) | —CH₂—⟨phenyl⟩ | 175–177 | toluene |
| (15) | ⟨phenyl⟩—CH₃ | 248–250 | toluene |

4-Hydroxyalkoxynaphthalimides (Table 2)

160 ml of ethylene glycol are initially placed in a stirred vessel, with the exclusion of atmospheric moisture, and 18.12 g of a methanolic solution of sodium methylate (29.8% strength) are added dropwise. The mixture is stirred for 2 hours at room temperature and the methanol is then distilled off at 60°–70° C. under a water pump vacuum. 28.77 g of N-n-butyl-4-chloronaphthalimide (12) are introduced at room temperature. The pale yellow reaction mixture is heated to 100° C., stirred for 3 hours at 100°–105° C., allowed to cool to room temperature and diluted with 160 ml of water. When the product has been filtered off with suction the filter cake is washed with water until it is neutral and free from chloride ions. It is dried at 60° C. in vacuo. 20.7 g of compound (22) are obtained, and after recrystallization from toluene this has a constant melting point of 127°–129°.

The compounds shown in Table 2 can be prepared analogously, it being necessary in individual cases to extend the reaction time to 10 hours.

TABLE 2

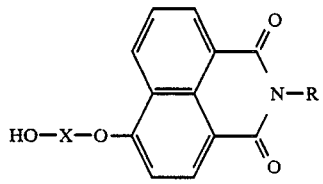

| No. | R | X | Melting point °C. | Purifying agent |
|---|---|---|---|---|
| (21) | —CH₃ | —CH₂CH₂— | 204–207 | methyl benzoate |
| (22) | —(CH₂)₃CH₃ | —CH₂CH₂— | 127–129 | toluene |
| (23) | —(CH₂)₃OCH₃ | —CH₂CH₂— | 144–146 | toluene |
| (24) | —CH₂—⟨phenyl⟩ | —CH₂CH₂— | 157–159 | ethyl acetate |
| (25) | ⟨phenyl⟩—CH₃ | —CH₂CH₂— | 278–280 | methyl benzoate |
| (26) | —CH₃ | —(CH₂)₃— | 164–167 | toluene |
| (27) | —CH₃ | —(CH₂)₄— | 166–168 | chlorobenzene |
| (28) | —CH₃ | —CH₂C(CH₃)₂CH₂— | 212–214 | chlorobenzene |
| (29) | —CH₃ | —CH₂CH₂OCH₂CH₂— | 135–137 | ethyl acetate |

Sulfuric acid ester-salts of the 4-hydroxyalkoxynaphthalimides 14.26 g of 4-(3-hydroxypropoxy)-N-methylnaphthalimide (26) are introduced at 5°–10° and in the course of 30 minutes into 33 ml of concentrated (96% strength) sulfuric acid with stirring. Stirring is continued at this temperature for 3 hours until a brownish-yellow, homogeneous solution has been formed and a small sample taken from it forms a clear solution in water. The mixture is then poured into 260 g of ice water and neutralized, with cooling, by concentrated sodium hydroxide solution. After 1 hour the precipitated sodium sulfate decahydrate is filtered off with suction at 10° and rinsed with ice water until the runnings are colorless. 80 g of sodium chloride are added to the filtrate (400 ml), the mixture is stirred at room temperature for 2 hours, the product is filtered off with suction and the material on the filter is washed free from sulfate ions by means of 20% strength NaCl solution. It is dried at 60° in vacuo. This gives 19.0 g of the following sulfuric acid ester-salt

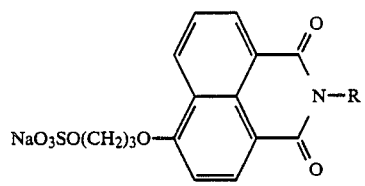

containing 7.5% of NaCl and 0.8% of water.

The 4-hydroxyalkoxynaphthalimides shown in Table 2 are converted into their sulfuric acid ester-salts analogously. The compounds thus prepared are listed in Table 3.

USE EXAMPLES

Example 1

10 g of polyamide-6 fabric were brightened in a laboratory dyeing apparatus using the compounds listed in Table 3.

Liquor composition

Liquor ratio: 1:20
0.25% of optical brightener, relative to the weight of the goods, 100% active substance,
2.0 g/l of sodium acetate,
1.0 ml/l of acetic acid and
0.5 g/l of nonylphenyl polyglycol ether The goods were introduced into the liquor at approx. 40° C., the beakers were inserted and the apparatus was then brought to 85° C. in the course of about 30 minutes. Treatment was carried out for a further 30 minutes at this temperature. The apparatus was then cooled to approx. 30° C. in about 30 minutes and the sections of fabric were taken out and rinsed vigorously at about 60° C. and then under cold conditions. After being centrifuged they were subjected to careful dry hot pressing.

The reflectance of the sections was determined using a DMC 25 reflectance spectrophotometer, and the whiteness values were calculated by the Ganz formula.

Example 2

10 g of polyamide 6 fabric were bleached and at the same time brightened in a laboratory dyeing apparatus, using the compounds listed in Table 3. The whiteness values obtained are coordinated in Table 3 with the results from Example 1. It was found that the substances according to the invention are resistant to chlorite. The whiteness values from Example 1 are exceeded throughout.

Liquor composition

Liquor ratio: 1:20
0.25% of optical brightener,
1.25 g/l of sodium chlorite (100% strength)
1.2 g/l of sodium nitrate,
1.2 g/l of bleaching auxiliary,
2.0 g/l of potassium hydrogen tartrate and
0.5 g/l of nonylphenyl oxyethylate The treatment of the fabric samples, in particular the temperature control, was effected in the same manner as that indicated in Example 1. The whiteness values derived from the reflectance values are shown in Table 3.

TABLE 3

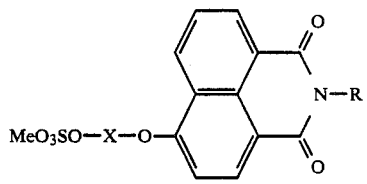

| No. | R | X | whiteness value (WV) without chlorite WV | shade | with chlorite WV | shade |
|---|---|---|---|---|---|---|
| (31) | —CH$_3$ | —CH$_2$CH$_2$— | 207 | 0.7 G | 224 | −0.1 B |
| (32) | —(CH$_2$)$_3$CH$_3$ | —CH$_2$CH$_2$— | 212 | 0.4 B | 227 | −0.1 B |
| (34) | —CH$_2$—C$_6$H$_5$ | —CH$_2$CH$_2$— | 201 | 1.1 G | 221 | 0.7 G |
| (36) | —CH$_3$ | —(CH$_2$)$_3$— | 218 | 0.9 G | 229 | 0.4 G |
| (37) | —CH$_3$ | —(CH$_2$)$_4$— | 217 | 1.0 G | 234 | 0.6 G |
| (38) | —CH$_3$ | —CH$_2$C(CH$_3$)$_2$CH$_2$— | 213 | 1.0 G | 226 | 0.1 B |

We claim:

1. A compound of the formula (1)

$$\text{MeO}_3\text{SO—X—O—[naphthalimide]—N—R}$$
(1)

in which
R denotes hydrogen, alkyl, alkoxyalkyl, cyclohexyl, methylcyclohexyl, benzyl, phenylethyl, phenyl, alkylphenyl or xylyl,
X denotes a C$_2$–C$_7$-alkylene group or a bridge member of the formula —X$^1$—(OX$^2$)$_n$— in which X$^1$ and X$^2$ denote C$_2$H$_4$ or C$_3$H$_7$ and n denotes 1 or 2 and Me denotes a proton, an alkali metal cation or a cation NH$_2$R$^1$R$^2$ in which R$^1$ and R$^2$ represent hydrogen, alkyl or hydroxyalkyl.

2. A compound of the formula 1 as claimed in claim 1, in which R denotes hydrogen, C$_1$–C$_4$-alkyl or benzyl, X denotes C$_2$–C$_5$-alkylene and Me denotes a proton, an alkali metal cation or a cation —NH$_2$R$^1$R$^2$ in which R$^1$ and R$^2$ represent hydrogen, C$_1$–C$_2$-alkyl or C$_1$–C$_2$-hydroxyalkyl.

* * * * *